US00PP17177P2

(12) United States Plant Patent
Vanderhaegen

(10) Patent No.: US PP17,177 P2
(45) Date of Patent: Oct. 31, 2006

(54) ***RHODODENDRON* PLANT NAMED 'KINKU SAKU'**

(50) Latin Name: ***Rhododendron simsii*×*Rhododendron stenopetalum linearifolium***
Varietal Denomination: Kinku Saku

(75) Inventor: Johan Vanderhaegen, Kruishoutem (BE)

(73) Assignee: Hortibreed NV, Lochristi (BE)

( * ) Notice: Subject to any disclaimer, the term of this patent is extended or adjusted under 35 U.S.C. 154(b) by 23 days.

(21) Appl. No.: 11/054,873

(22) Filed: Feb. 10, 2005

(51) Int. Cl.
*A01H 5/00* (2006.01)

(52) U.S. Cl. ..... Plt./239

(58) Field of Classification Search ..... Plt./238, Plt./239, 240
See application file for complete search history.

*Primary Examiner*—Kent Bell

(57) ABSTRACT

A new cultivar of *Rhododendron* plant named 'Kinku Saku' that is characterized by long linear dark shiny green leaves, good leaf retention, long palmately compound shaped single pink flowers and long flower life.

1 Drawing Sheet

Botanical classification: *Rhododendron simsii*×*Rhododendron stenopetalum linearifolium.*
Variety denomination: 'Kinku Saku'.

BACKGROUND OF THE INVENTION

The present invention relates to a new and distinct cultivar of *Rhododendron* plant botanically known as *Rhododendron* and hereinafter referred to by the cultivar name 'Kinku Saku'.

'Kinku Saku' is a hybrid that originated from the hybridization of the female or seed parent an unnamed proprietary *Rhododendron simsii* (not patented) and the male or pollen parent an unnamed proprietary *Rhododendron stenopetalum linearifolium* (not patented). The cultivar 'Kinku Saku' was selected by the inventor in 1997 as a single plant within the progeny of the stated cross in a cultivated area of Kruishoutem, Belgium.

Asexual reproduction of the new cultivar 'Kinku Saku' by cuttings was first performed in 2000 in Kruishoutem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'Kinku Saku'. These traits in combination distinguish 'Kinku saku' as a new and distinct cultivar apart from all other existing varieties of *Rhododendron* known to the inventor.

1. *Rhododendron* 'Kinku Saku' exhibits long linear dark shiny green leaves.
2. *Rhododendron* 'Kinku Saku' exhibits good leaf retention.
3. *Rhododendron* 'Kinku Saku' exhibits long palmately compound shaped single pink flowers.
4. *Rhododendron* 'Kinku Saku' exhibits a long flower life.

The new cultivar 'Kinku Saku' is distinguishable from the female parent an unnamed *Rhododendron simsii* by the following characteristics:

1. 'Kinku Saku' has linear shaped leaves. The leaves of the female parent have an elliptic shape.
2. 'Kinku Saku' has long palmately compound shaped single pink flowers. The flowers of the female parent are star shaped and double.

The new cultivar 'Kinku Saku' is distinguishable from the male parent an unnamed *Rhododendron stenopetalum linearifolium* by the following characteristics:

1. 'Kinku Saku' has good leaf retention. The leaves of the male parent are subject to leaf drop.
2. 'Kinku Saku' has longer flower longevity.

The closest comparison cultivar is the male parent plant an unnamed *Rhododendron stenopetalum linearifolium.*

BRIEF DESCRIPTION OF THE DRAWING

The accompanying photograph illustrates the distinguishing traits of *Rhododendron* 'Kinku Saku'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'Kinku Saku'. Data was collected in Kruishoutem, Belgium from 24 month old glass greenhouse grown plants in 14 cm. containers. The time of year was Winter and the average daytime temperature was 20° Centigrade during the Summer and 3° Centigrade during the Winter. The average nighttime temperature was 12° Centigrade during the Summer and 0° Centigrade during the Winter. The light level was natural outdoor light and there were no photoperiodic treatments. Color determinations are in accordance with The Royal Horticultural Society Colour Chart 2001 edition, except where general color terms of ordinary dictionary significance are used. The growing requirements are similar to the species. 'Kinku Saku' has not been tested under all possible conditions and phenotypic differences may be observed with variations in environmental, climatic, and cultural conditions, however, without any variance in genotype.

Botanical classification: *Rhododendron* 'Kinku Saku'.
Use: Ornamental Perennial.
Parentage: 'Kinku Saku' is a hybrid that resulted from the hybridization of the following plants: Female or seed parent an unnamed proprietary *Rhododendron simsii.* Male or pollen parent an unnamed proprietary *Rhododendron stenopetalum linearifolium.*
Vigor: Moderate.
Growth rate: Approximately 8 to 15 cm. per year.
Growth habit: Broad upright, densely branched.
Plant shape: Broad inverted triangle.
Suitable container size: 1.0 liter container.
Height: Average 23.5 cm. in height.
Width: Average 42 cm. in width.
Hardiness: USDA Zone 9.
Propagation: Cuttings.
Time to initiate roots: Approximately 30 days to produce roots on an initial cutting.
Time to produce a rooted cutting or liner: Approximately 60 days.
Root system: Fine and fibrous.
Stem:
- *Branching habit.*—Freely branching.
- *Average number of lateral branches.*—36.
- *Pinching.*—Yes.
- *Lateral branch diameter.*—3 mm. in diameter.
- *Lateral branch length.*—11.3 cm. in length.
- *Lateral branch strength.*—Moderately strong.
- *Stem color.*—144A, older stems 165A.
- *Pubescence.*—Dense, length 1.0 mm, color 172C to 172D.
- *Internode length.*—1 cm. between nodes.
- *Shape.*—Round.
- *Surface.*—Dull.
- *Stem strength.*—Strong.

Foliage:
- *Texture.*—Glossy, slightly rugose.
- *Leaf arrangement.*—Alternate, clustered towards the top of the stems.
- *Compound or single.*—Single.
- *Quantity of leaves per lateral branch.*—28.
- *Leaf shape.*—Linear.
- *Leaf apex.*—Acute.
- *Leaf base.*—Attenuate.
- *Leaf length.*—4.5 cm. in length.
- *Leaf width.*—7.0 mm. in width.
- *Pubescence.*—Slight, both sides, length 1 mm, color gray-orange N172D.
- *Leaf margin.*—Entire.
- *Vein pattern.*—Pinnate.
- *Young leaf color* (*upper surface*).—137C.
- *Young leaf color* (*lower surface*).—143A.
- *Mature leaf color* (*upper surface*).—139A.
- *Mature leaf color* (*lower surface*).—137C to 137D.
- *Vein color* (*lower surface*).—144A.
- *Vein color* (*upper surface*).—144A.
- *Leaf attachment.*—Petiolate.
- *Petiole dimensions.*—9 mm. in length and 2 mm. in diameter.
- *Petiole color.*—144A.
- *Durability of foliage to stress.*—High.

Flower:
- *Flower arrangement.*—Terminal clusters.
- *Inflorescence type.*—Single.
- *Inflorescence dimensions.*—8.7 cm. in diameter and 4.3 cm. in height.
- *Flowering habit.*—Continuously once a year.
- *Quantity of flowers per lateral stem.*—Approximately 5.
- *Quantity of flower buds per lateral stem.*—Approximately 5.
- *Quantity of flowers and buds per plant.*—Approximately 180.
- *Flowering season.*—Late winter to early summer.
- *Time to flower or response time.*—10.5 months.
- *Rate of flower opening.*—After the first flower of a cluster has opened, all flowers of that cluster will open in approximately 14 days.
- *Fragrance.*—None.
- *Self-cleaning or persistent.*—Self-cleaning.
- *Flower bud length.*—8 mm. in length.
- *Flower bud diameter.*—7 mm. in diameter.
- *Flower bud shape.*—Broad ovate.
- *Bud color.*—144B.
- *Rate of bud opening.*—14 days.
- *Flower aspect.*—Upright to outward.
- *Flower shape.*—Long palmately compound.
- *Flower dimensions.*—Average 7.0 cm. in diameter and 5.6 cm. in height.
- *Flower longevity.*—Lasts approximately 14 days on plant.
- *Petal appearance.*—Slightly glossy, slight velvety.
- *Petal texture.*—Glabrous.
- *Petal arrangement.*—Irregular rotate.
- *Number of petals.*—Five in number.
- *Petals fused or unfused.*—Unfused.
- *Petal shape.*—Linear.
- *Petal margin.*—Entire.
- *Petal apex.*—Obtuse.
- *Petal base.*—Attenuate.
- *Petal dimensions.*—Average 5.5 cm. in length and 5 mm. in width.
- *Petal color when opening* (*upper side*).—58C.
- *Petal color when opening* (*under side*).—58C.
- *Petal color when fully opened* (*upper side*).—58C.
- *Petal color when fully opened* (*under side*).—58C.
- *Petal color fading to.*—Fading to 58D.

Calyx:
- *Calyx shape.*—Funnelform.
- *Calyx dimensions.*—1.0 cm. in length and 1.5 cm. in diameter.

Bracts:
- *Number of bracts.*—8 in number.
- *Bract dimensions.*—0.8 cm. in length and 0.3 cm. in width.
- *Bract shape.*—Linear.
- *Bract apex.*—Acute.
- *Bract pubescence.*—Sparsely covered, color N155B.
- *Bract color* (*both sides*).—144A.

Reproductive organs:
- *Stamen number.*—5.
- *Anther shape.*—Dorsifixed, oval.
- *Anther size.*—2 mm. in length.
- *Anther color.*—53B.
- *Amount of pollen.*—Very low.

*Pistil number.*—1.
*Pistil dimensions.*—2.6 cm. in length.
*Stigma shape.*—Club shaped, flattened at the top.
*Stigma color.*—183C.
*Style length.*—2.5 cm.
*Style color.*—59B.
*Ovary color.*—144B to 144C.

Seed: Seed production has not been observed.

Disease and pest resistance: Plants of the new *Rhododendron* have not been observed for disease or pest resistance.

It is claimed:

1. A new and distinct variety of *Rhododendron* plant named 'Kinku Saku' as described and illustrated.

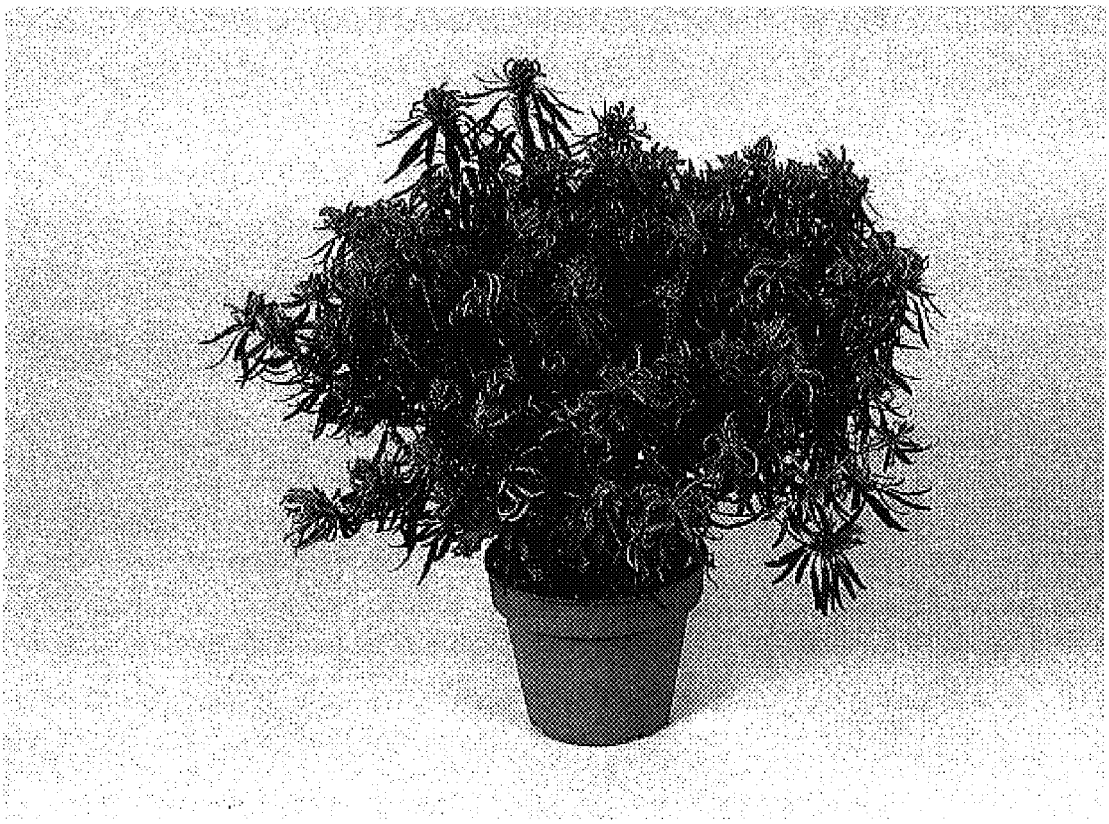

* * * * *